(12) United States Patent  
Yazaki et al.

(10) Patent No.: US 11,369,993 B2  
(45) Date of Patent: Jun. 28, 2022

(54) ULTRASONIC DIAGNOSTIC APPARATUS

(71) Applicant: HITACHI, LTD., Tokyo (JP)

(72) Inventors: Toru Yazaki, Tokyo (JP); Takuma Nishimoto, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 297 days.

(21) Appl. No.: 16/646,202

(22) PCT Filed: Sep. 28, 2018

(86) PCT No.: PCT/JP2018/036276  
§ 371 (c)(1),  
(2) Date: Mar. 11, 2020

(87) PCT Pub. No.: WO2019/181021  
PCT Pub. Date: Sep. 26, 2019

(65) Prior Publication Data  
US 2020/0275911 A1  Sep. 3, 2020

(30) Foreign Application Priority Data  
Mar. 23, 2018  (JP) .............................. JP2018-057097

(51) Int. Cl.  
*B06B 1/02*  (2006.01)  
*A61B 8/00*  (2006.01)  
(Continued)

(52) U.S. Cl.  
CPC .......... *B06B 1/0207* (2013.01); *A61B 8/4494* (2013.01); *A61B 8/54* (2013.01);  
(Continued)

(58) Field of Classification Search  
CPC ... B06B 1/0207; B06B 1/0215; B06B 1/0622; B06B 2201/76; A61B 8/4494; A61B 8/54; A61B 8/00; G01S 7/5201  
See application file for complete search history.

(56) References Cited

U.S. PATENT DOCUMENTS 5,424,546 A    6/1995  Okada et al.  
8,022,906 B2 * 9/2011  Yang .................... G09G 3/3283  
                                                      345/77

(Continued)

FOREIGN PATENT DOCUMENTS

JP    2008-252436 A    10/2008  
WO    2016/114018 A1    7/2016

OTHER PUBLICATIONS

International Search Report of PCT/JP2018/036276 dated Dec. 25, 2018.

*Primary Examiner* — Suman K Nath  
(74) *Attorney, Agent, or Firm* — Mattingly & Malur, PC

(57) ABSTRACT

The ultrasonic diagnostic apparatus includes: a transducer; a driving signal generation unit configured to generate a driving signal; and a transmission circuit configured to output a driving current corresponding to the driving signal, so as to drive the transducer, the transmission circuit includes: a transducer driving unit formed by a current mirror with a low voltage transistor and a high voltage transistor, the high voltage transistor being connected with the transducer, and a current source configured to supply an operation current corresponding to the driving signal to the low voltage transistor of the transducer driving unit, the driving signal generation unit includes: a transmission circuit driving unit replica that has a configuration same as that of the transducer driving unit, and a feedback control unit to (Continued)

detect a current flowing through a high voltage transistor of the transmission circuit driving unit replica, and to control the current to be constant.

15 Claims, 9 Drawing Sheets

(51) Int. Cl.
*B06B 1/06* (2006.01)
*G01S 7/52* (2006.01)

(52) U.S. Cl.
CPC .......... *B06B 1/0215* (2013.01); *B06B 1/0622* (2013.01); *B06B 2201/76* (2013.01); *G01S 7/52019* (2013.01)

(56) References Cited

U.S. PATENT DOCUMENTS

2008/0238532 A1  10/2008  Hanazawa et al.
2017/0370886 A1* 12/2017  Nishimoto ............. G01N 29/30

* cited by examiner

[FIG. 1]
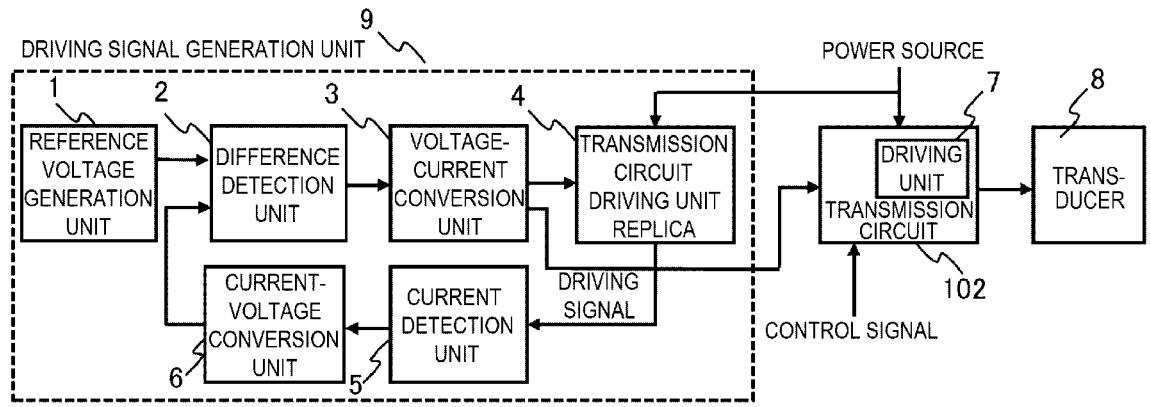
[FIG. 2]
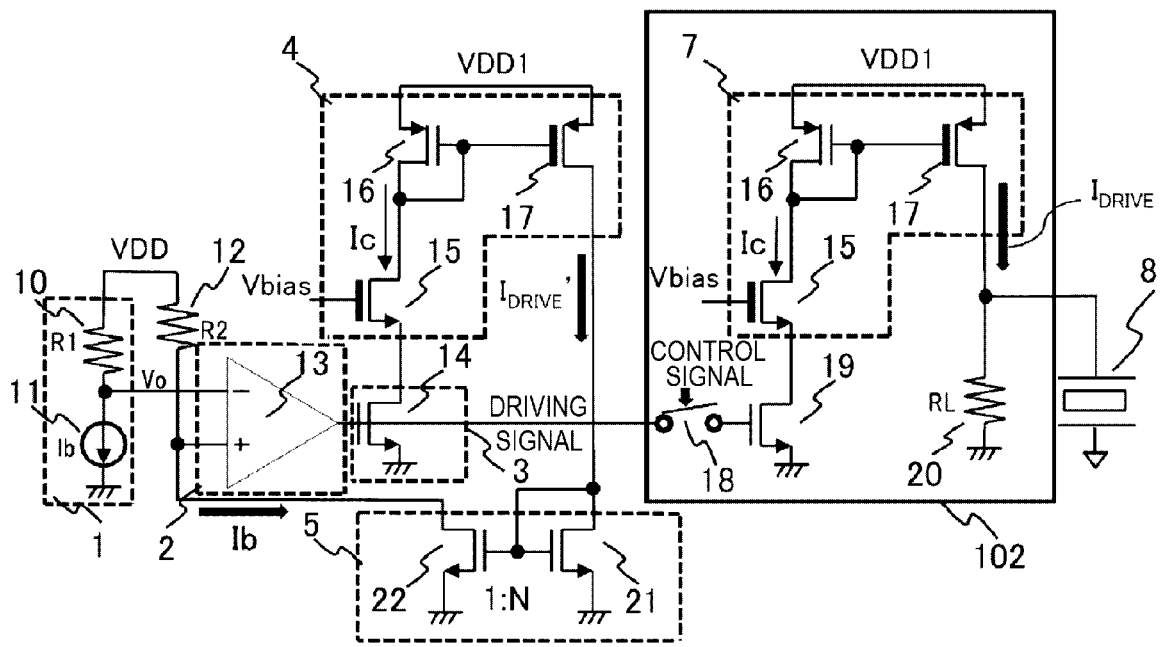

[FIG. 3]
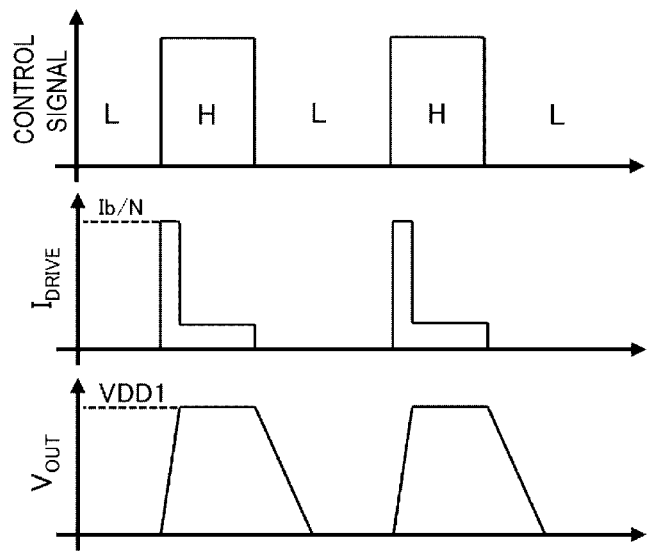
[FIG. 4]
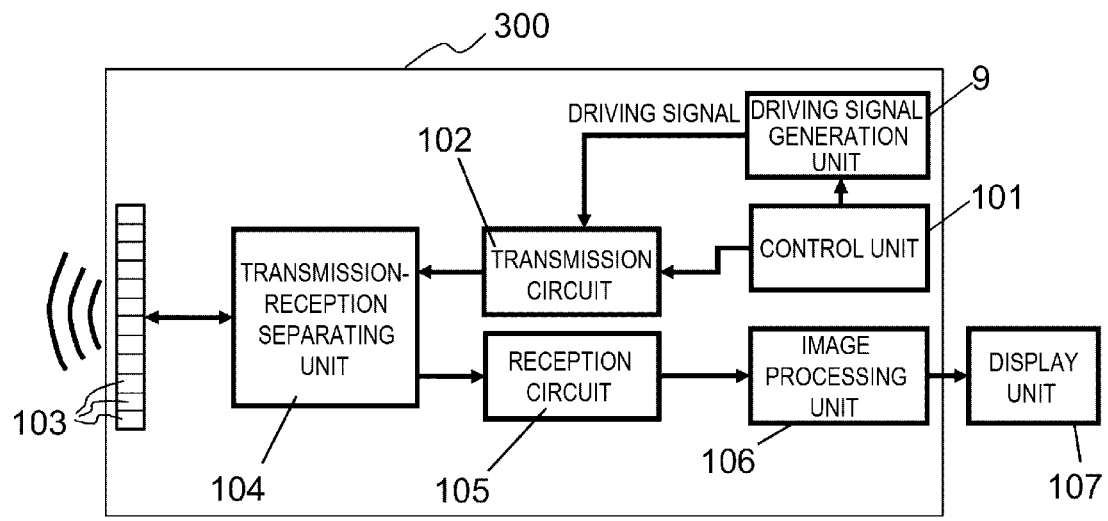

[FIG. 5]
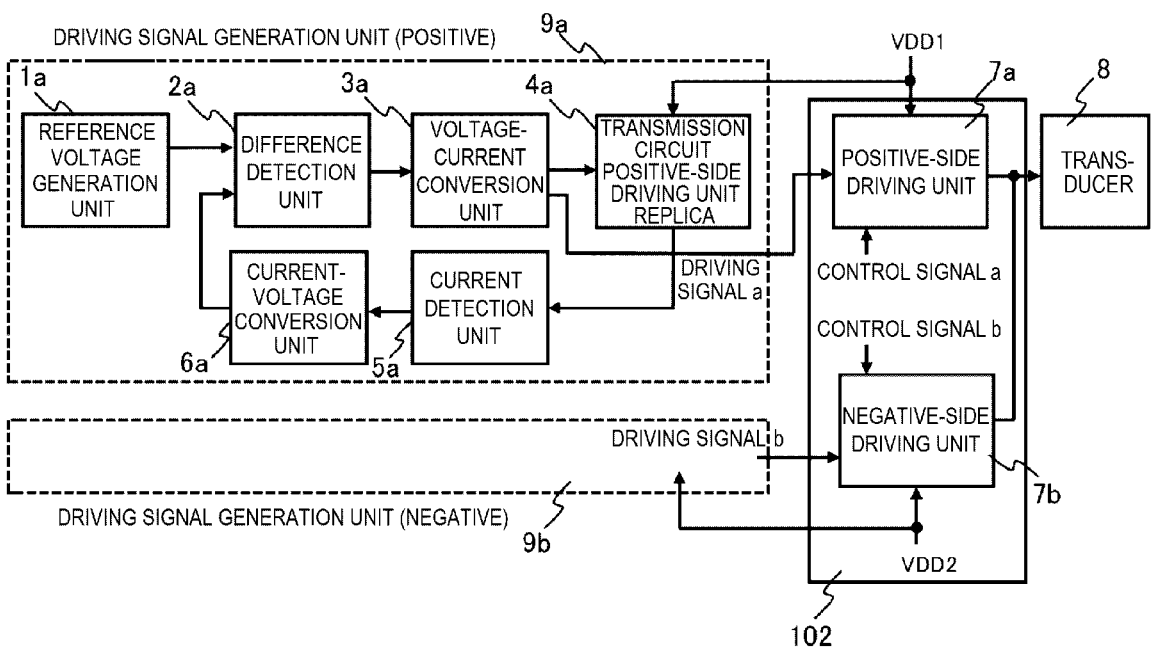

[FIG. 6]
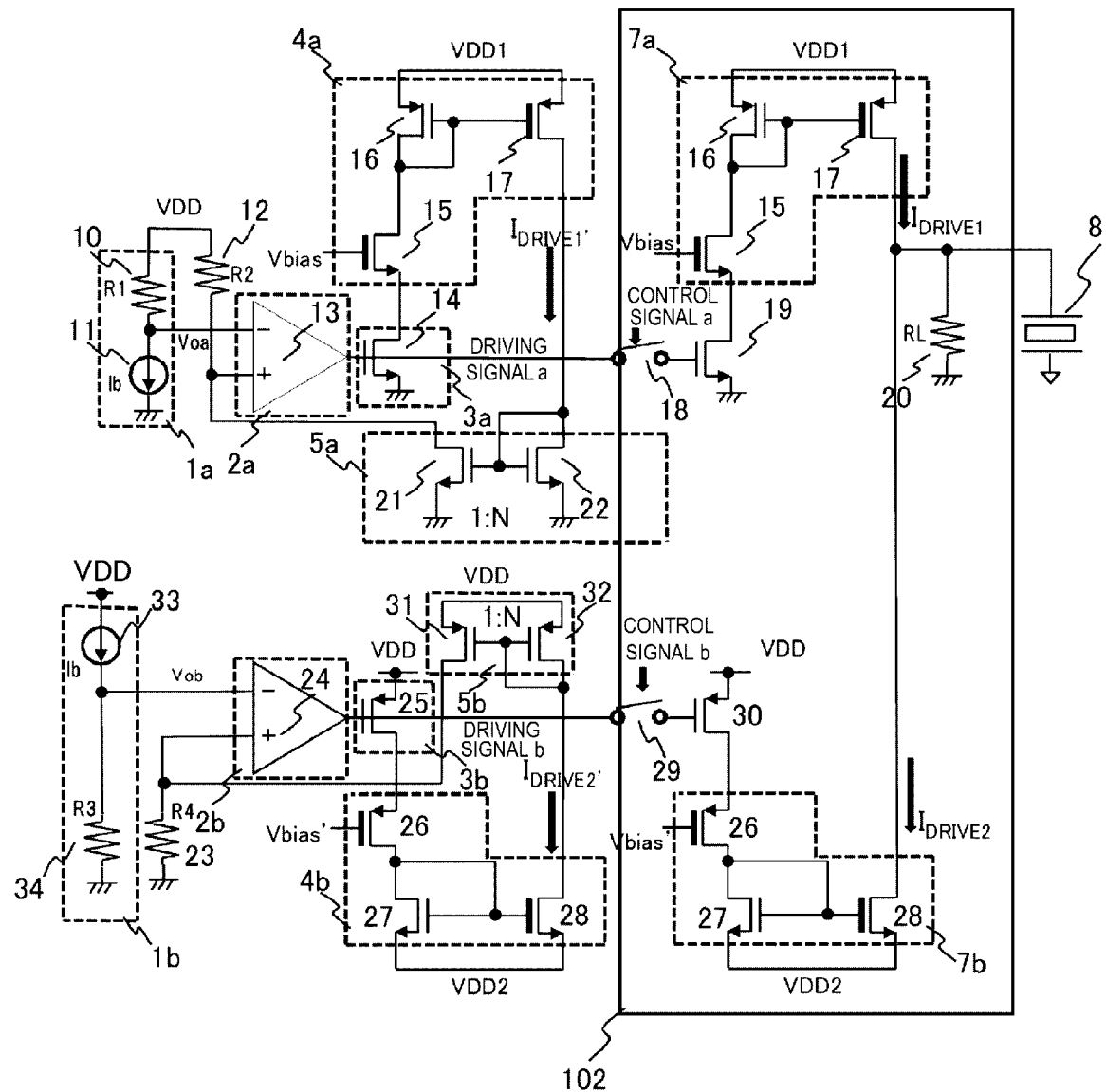

[FIG. 7]
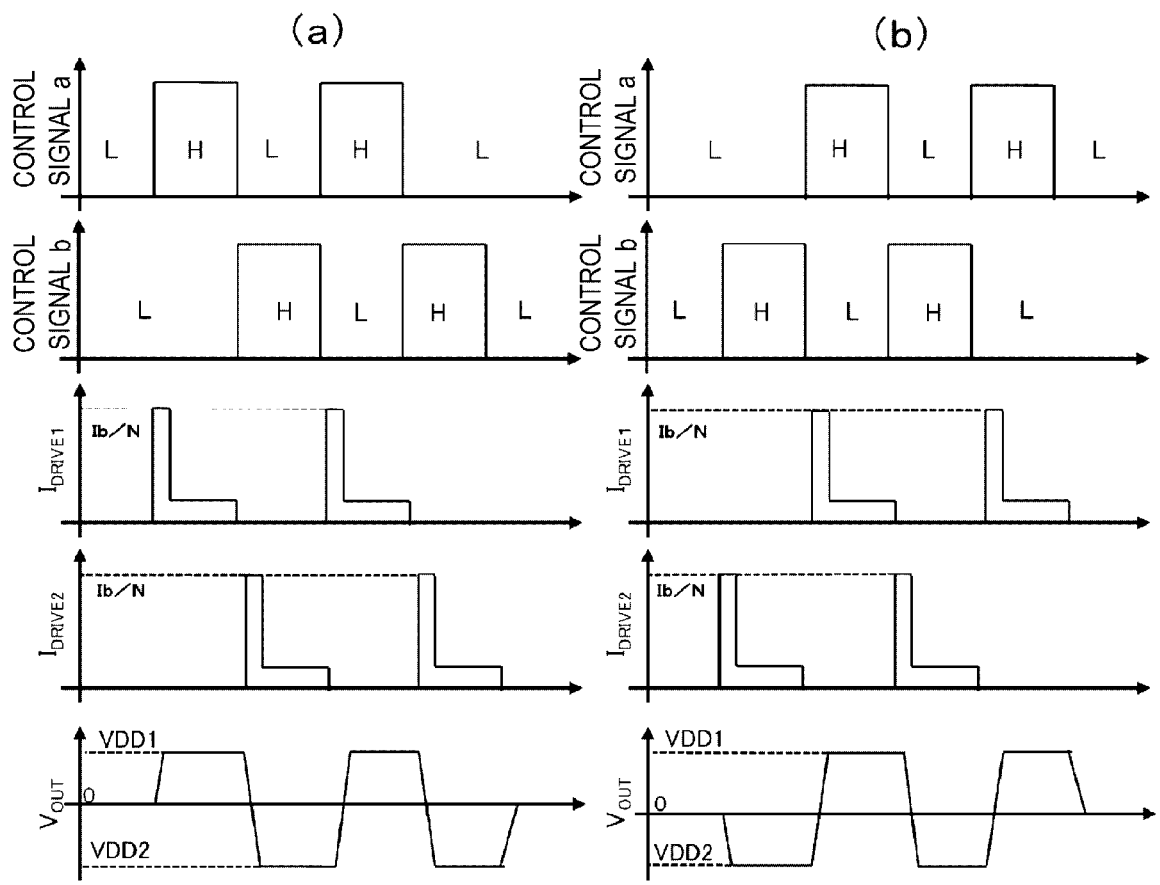

[FIG. 8]
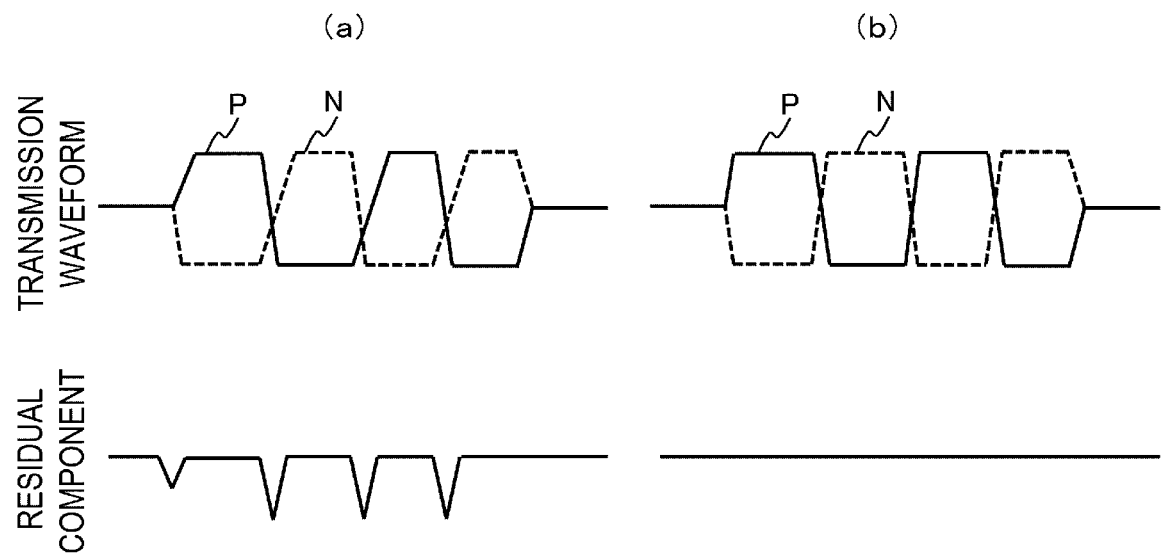
[FIG. 9]
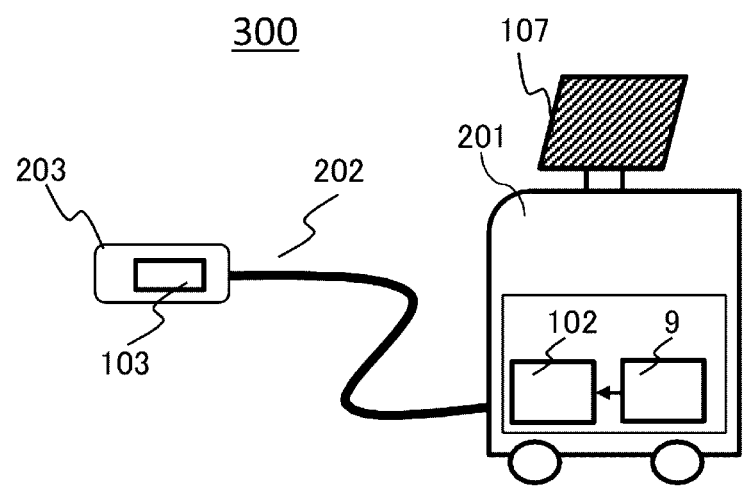

[FIG. 10]
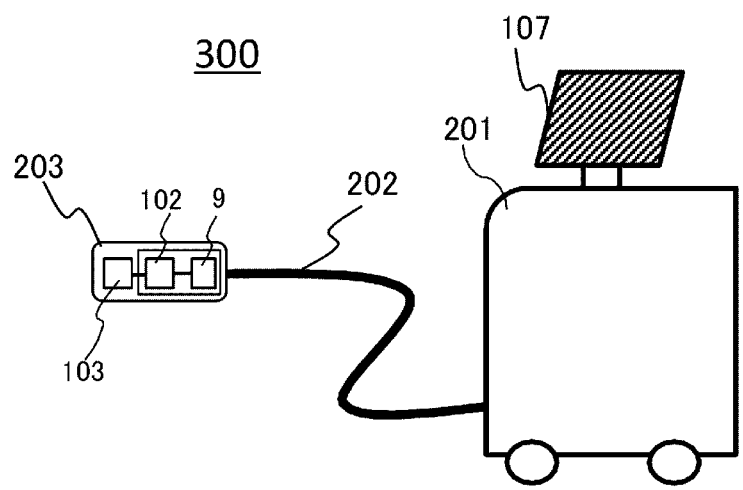

[FIG. 11]
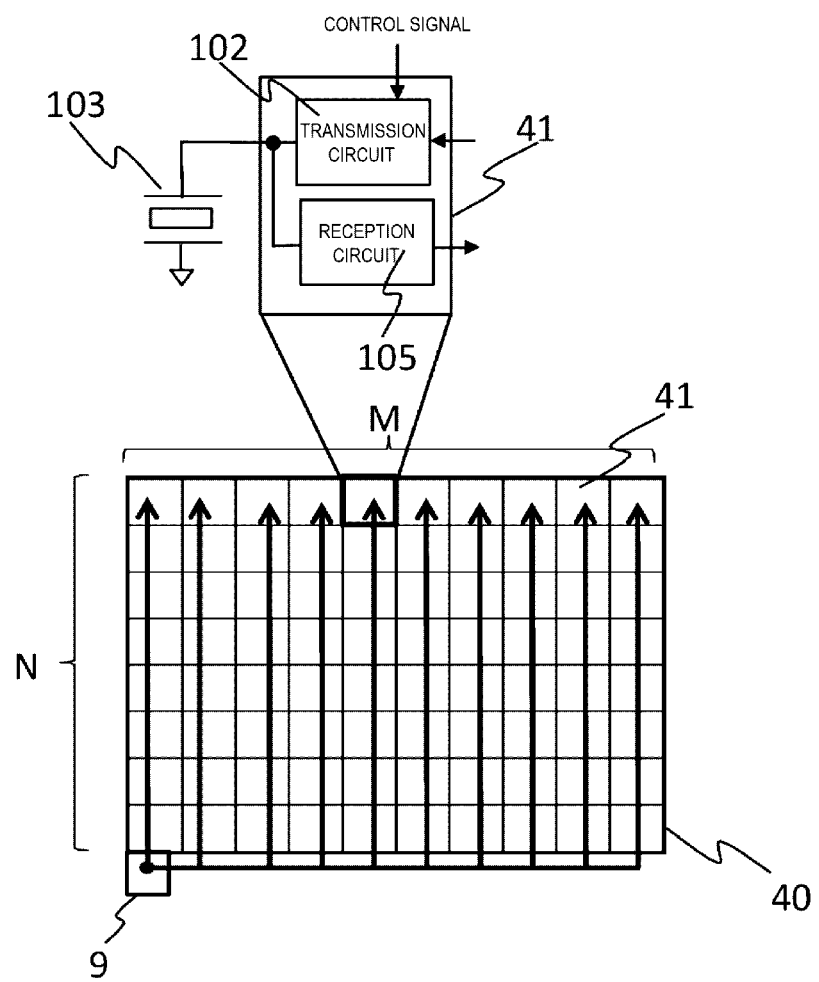

[FIG. 12]
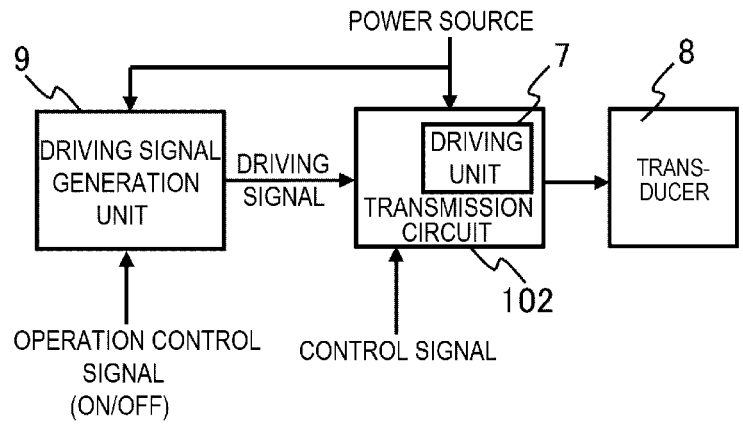
[FIG. 13]
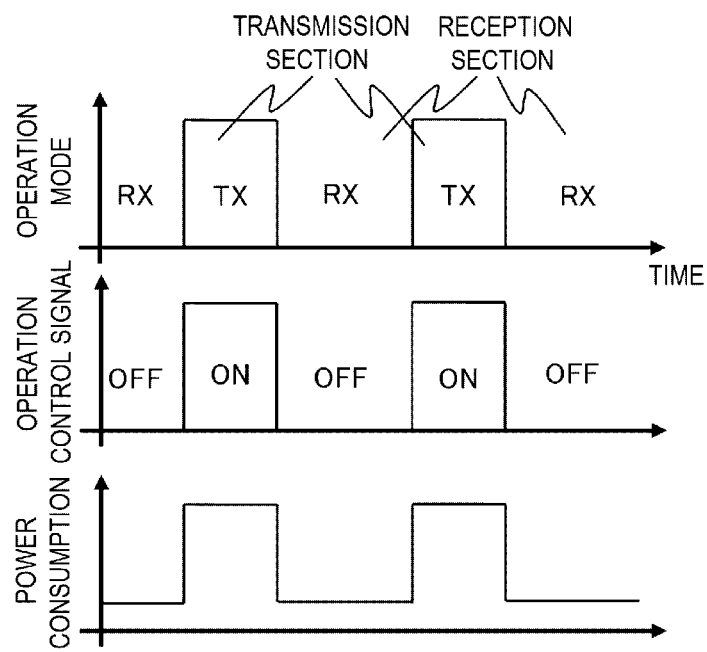

ULTRASONIC DIAGNOSTIC APPARATUS

TECHNICAL FIELD

The present invention relates to an ultrasonic diagnostic apparatus.

BACKGROUND ART

In an ultrasonic diagnostic apparatus, there is an imaging method referred to as tissue harmonic imaging (THI) that images a distortion component generated in a living body, in comparison with a normal Brightness (B) mode imaging, since a harmonic component is used, influences of side lobes and artifacts generated in a fundamental wave can be reduced, and high image quality can be achieved. The THI includes two kinds of methods: a filter method in which only a secondary distortion component generated in the living body is extracted with a filter, and a pulse inversion method in which a fundamental wave component is removed by adding positive and negative symmetric waves. In the filter method, an image can be captured by performing transmission and reception for one time, but it is necessary to separate the fundamental wave component and the harmonic component, and thus, a narrow-band transmission waveform is required and a space disintegration capacity is reduced. On the other hand, it is known that in the pulse inversion method, capturing an image requires two times of transmission and reception, but separation of the fundamental wave component and the harmonic component is not required, so that broadband transmission is possible and the space disintegration capacity is improved. The adoption of THI using the pulse inversion method in the ultrasonic diagnostic apparatus currently becomes a mainstream.

CITATION LIST

Patent Literature

PTL 1: WO 2016/114018

SUMMARY OF INVENTION

Technical Problem

In the THI using the pulse inversion method, positive-negative symmetry of transmission waveforms is important. Since positive and negative transmission and reception signals are added, when rises and falls of the transmission waveforms are different, cancellation remnant after the addition causes deterioration of the image. In particular, it is known that in a pulse transmission circuit that generate high and low discrete signals, since the discrete signals are generated by using PMOS transistors and NMOS transistors with different transistor polarities, the waveforms becomes positive-negative asymmetric due to the process variation of a semiconductor.

PTL 1 discloses a technique in which a replica having the same configuration as a transmission circuit driving unit configured with a low voltage transistor and a high voltage transistor is prepared, a sum of currents flowing therethrough is kept constant, so that a driving current is constant with respect to the process variation. However, in the PTL 1, although the sum of the currents of the low voltage transistor and the high voltage transistor of the replica unit is constant, a current ratio (mirror ratio) flowing through the low voltage transistor and the high voltage transistor changes due to the process variation of the semiconductor, and therefore, the current flowing through the high voltage transistor in the transmission circuit driving unit, that is, the driving current is not constant, and it is difficult to form a symmetrical waveform with high accuracy.

Therefore, an object of the invention is to provide an ultrasonic diagnostic apparatus in which a driving current of a transducer is constant with respect to a process variation of a semiconductor.

Solution to Problem

In order to solve the above problems, one example of an "ultrasonic diagnostic apparatus" according to the invention is given.

The ultrasonic diagnostic apparatus includes: ultrasonic diagnostic apparatus includes: a transducer; a driving signal generation unit configured to generate a driving signal; and a transmission circuit configured to output a driving current corresponding to the driving signal, so as to drive the transducer, in which the transmission circuit includes: a transducer driving unit formed by a current mirror with a low voltage transistor and a high voltage transistor, the high voltage transistor being connected with the transducer, and a current source configured to supply an operation current corresponding to the driving signal to the low voltage transistor of the transducer driving unit, the driving signal generation unit includes: a transmission circuit driving unit replica that has a configuration same as that of the transducer driving unit, and a feedback control unit configured to detect a current flowing through a high voltage transistor of the transmission circuit driving unit replica, and to control the current to be constant, and a signal applied from the feedback control unit to a current source configured to supply an operation current to a low voltage transistor of the transmission circuit driving unit replica is supplied, as the driving signal, to the current source configured to supply the operation current to the low voltage transistor of the transducer driving unit.

Advantageous Effect

According to the invention, the driving current of the transducer can be constant with respect to a process variation of a semiconductor.

Problems, configurations, and effects other than those described above will become apparent from the following description of the embodiments.

BRIEF DESCRIPTION OF DRAWINGS

FIG. 1 is a block configuration diagram of a driving signal generation unit and a transmission circuit according to a first embodiment of the invention.

FIG. 2 is an example of a detailed circuit diagram of FIG. 1.

FIG. 3 is a diagram illustrating control signals and transmission waveforms of the transmission circuit of FIG. 1.

FIG. 4 is a diagram illustrating a configuration example of an ultrasonic diagnostic apparatus according to the first embodiment.

FIG. 5 is a block configuration diagram of a driving signal generation unit and a transmission circuit according to a second embodiment of the invention.

FIG. 6 is an example of a detailed circuit diagram of FIG. 5.

FIG. 7 is a diagram illustrating control signals and transmission waveforms of the transmission circuit of FIG. 5.

FIG. 8(a) is a diagram showing a transmission waveform and a residual component of pulse inversion in a case where a driving signal generation unit is not provided, and FIG. 8(b) is a diagram showing a transmission waveform and a residual component of pulse inversion in a case where the driving signal generation unit is provided.

FIG. 9 is a diagram illustrating a configuration example of an ultrasonic diagnostic apparatus according to a third embodiment of the invention.

FIG. 10 is a diagram illustrating a configuration example of an ultrasonic diagnostic apparatus according to a fourth embodiment of the invention.

FIG. 11 is a diagram illustrating a configuration example of a transmission circuit of FIG. 10.

FIG. 12 is a diagram illustrating a configuration example of an ultrasonic diagnostic apparatus according to a fifth embodiment of the invention.

FIG. 13 is a diagram illustrating an operation mode and power consumption of the ultrasonic diagnostic apparatus of FIG. 12.

DESCRIPTION OF EMBODIMENTS

In the following embodiments to be described below, description may be divided into a plurality of sections or embodiments if necessary for convenience, unless particularly demonstrated, these embodiments are not independent with each other, but in a relationship in which one embodiment is a variation, detailed description, supplementary description, or the like of a part or all of another embodiment. In the following embodiments, when a number and the like (including number of article, numeric value, quantity, range and the like) of an element is referred to, these parameters are not limited to the specific numbers, and the values may be greater or less than these specific numbers, unless otherwise specified or unless the specific numbers are clearly limited to specific numbers in principle.

Further, in the embodiments described below, it is needless to say that the constituent element (including element steps) are not always indispensable unless otherwise stated or except the case where the components are apparently indispensable in principle. Similarly, in the following embodiments, when referring to shapes, positional relationships, and the like of the constituent elements and the like, shapes and the like which are substantially approximate or similar to those are included, unless particularly specified or considered to be apparently excluded in principle. The same also applies to the numerical value and the range described above.

Hereinafter, embodiments of the invention will be described in detail based on drawings. In all the drawings for describing the embodiments, the same members are denoted by the same reference numerals in principle, and the repetitive description thereof will be omitted.

An ultrasonic diagnostic apparatus is widely used as a medical diagnosis apparatus that can be non-invasively observed in real time. Further, in recent years, in addition to a two-dimensional image in related art, a three-dimensional stereoscopic image and the like can also be displayed, and application thereof are continuously expanding. Meanwhile, since image quality is lower than that of an X-ray computed tomography (CT) apparatus or a magnetic resonance imaging (MRI) apparatus, higher image quality than ever before is required. Hereinafter, examples in which this invention is applied to an ultrasonic diagnostic apparatus are described.

First Embodiment

FIG. 1 is a block configuration diagram illustrating a driving signal generation unit and a transmission circuit according to a first embodiment of the invention. A driving unit 7 provided in a transmission circuit 102 and driving a transducer 8 is configured to output a driving current corresponding to a driving signal supplied from a driving signal generation unit 9 so as to drive the transducer 8. At this time, a control signal is input to the transmission circuit 102, and the driving signal is turned on and off according to this control signal, so that the driving current flows to output, and High and Low signals can be generated.

The driving signal generation unit 9 is configured with a reference voltage generation unit 1, a difference detection unit 2, a voltage-current conversion unit 3, a transmission circuit driving unit replica 4, a current detection unit 5, and a current-voltage conversion unit 6. The difference detection unit 2, the voltage-current conversion unit 3, the transmission circuit driving unit replica 4, the current detection unit 5, and the current-voltage conversion unit 6 constitute a feedback control unit, and an output voltage of the difference detection unit 2 is converted to a current by the voltage-current conversion unit 3 and is transmitted to the transmission circuit driving unit replica 4. The transmission circuit driving unit replica 4 generates a driving current in the same manner as the transmission circuit driving unit 7, the driving current flows through the current detection unit 5 and is converted to a voltage signal by the current-voltage conversion unit 6, and the voltage signal is returned to the difference detection unit 2. At this time, a voltage equal to a reference voltage is finally input to an input of the difference detection unit 2 due to a feedback effect. That is, an output voltage of the current-voltage conversion unit 6 is equal to a reference voltage of the reference voltage generation unit 1. Since the current to the current-voltage conversion unit 6 is the driving current transmitted from the current detection unit 5, the driving current has a constant value. A current for generating the driving current is the output current of the voltage-current conversion unit 3, and the current is input to the transmission circuit 102 as a driving signal, so that the driving current output from the transmission circuit 102 is kept constant.

FIG. 2 illustrates a detailed configuration example. The transmission circuit 102 is configured with an NMOS transistor 19 that converts a driving signal into a current, a switch 18 that turns on and off the driving signal by a control signal, a driving unit 7, and a load resistor 20. The driving unit 7 is configured with a current mirror including a high voltage NMOS transistor 15 that is a level shift for NMOS transistor 19 protection for applying a high voltage power source VDD1, a low voltage PMOS transistor 16 and a high voltage PMOS transistor 17. The NMOS transistor 19 that converts the driving signal into the current can be said to be a current source that causes an operation current corresponding to the driving current to flow through the low voltage PMOS transistor 16.

In the driving signal generation unit 9, the reference voltage generation unit 1 is configured with a resistor 10 and a current source 11. The difference detection unit 2 includes an OPAMP 13, and an output of the OPAMP 13 is connected to the voltage-current conversion unit 3. The voltage-current conversion unit 3 converts an output voltage from the OPAMP 13 into a current by an NMOS transistor 14, and inputs the current to the driving unit replica 4. The driving current output from the driving unit replica 4 is output from the current detection unit 5 configured with a current mirror including NMOS transistors 21, 22. This current is converted into a voltage again by a resistor 12 which is the current-voltage conversion unit 6 and is input to the difference detection unit 2. The NMOS transistor 14 can be said to be a current source that causes the operation current to flow through the low voltage PMOS transistor 16 of the transmission circuit driving unit replica 4.

More detailed operations will be described. A minus terminal of the OPAMP 13 is connected to a current source 11 and one side of the resistor 10 connected to a power source VDD, and a plus terminal of the OPAMP 13 is connected to one side terminal of the resistor 12 connected to the power source VDD and a drain terminal of an NMOS transistor 22 of the current detection unit 5. At this time, when a voltage of the minus terminal of the OPAMP13 is Vo, the plus terminal of the OPAMP13 becomes VDD in an initial state if a current of the NMOS transistor 22 is zero. Since the output of the OPAMP 13 becomes high and the NMOS transistor 14 is turned on, a current Ic is supplied from a drain terminal of the NMOS transistor 14 and is input to the driving unit replica 4. An $I_{DRIVE}'$ is output from an output of the driving unit replica 4 and is input to the current detection unit 5. The NMOS transistors 21 and 22 of the current detection unit 5 is a current mirror with a mirror ratio of N:1, a current of $I_{DRIVE}'/N$ from the drain terminal of the NMOS transistor 22 is applied to the resistor 12 which is the current-voltage conversion unit 6. At this time, since a series of operations are negative feedback operations, the plus terminal and the minus terminal of the OPAMP 13 are automatically controlled so as to have a same potential. That is, the plus terminal of the OPAMP 13 is Vo. When resistance values of the resistor 10 and the resistor 12 are equal, Ib equal to that of the current source 11 is supplied from the drain of the NMOS transistor 22. Since the current mirror ratio of the NMOS transistors of the current detection unit 5 is N:1, $I_{DRIVE}'$ is expressed by Equation (1).

[Equation 1]

$$I_{DRIVE}' = Ib \times N \quad (1)$$

At this time, when a mirror ratio of the low voltage transistor 16 and the high voltage transistor 17 of the driving unit replica 4 is M, a current supplied from the NMOS transistor 14 to the PMOS transistor 16 of the driving unit replica 4 is expressed by Equation (2).

[Equation 2]

$$Ic = I_{DRIVE}'/M = (Ib \times N)/M \quad (2)$$

When the switch 18 is turned on, the same potential as that of the NMOS transistor 14 of the driving signal generation unit 9 is input to a gate terminal of the NMOS transistor 19 of the transmission circuit 102 as the driving signal. Therefore, a current same as the Ic which is input to the driving unit replica 4 of the driving signal generation unit 9 from the drain terminal of the NMOS transistor 14 is also input to the transmission circuit driving unit 7. Since the transmission circuit driving unit 7 is also configured with the same low voltage PMOS transistor 16 and the high voltage PMOS transistor 17 as that of the driving unit replica 4, when the mirror ratio is M, $I_{DRIVE}$ is expressed by Equation (3).

[Equation 3]

$$I_{DRIVE} = M \times Ic = Ib \times N \quad (3)$$

That is, the driving current is determined only by the current value Ib of the current source 11 and the mirror ratio of the current detection unit 5, and even when the mirror ratio M of the low voltage PMOS transistor 16 to the high voltage PMOS transistor 17 of the driving unit replica 4 changes due to process variations or the like, the driving current $I_{DRIVE}$ remains constant.

At this time, the same power source VDD1 is applied to the driving unit replica 4 and the driving unit 7, and the high voltage NMOS transistor 15 is provided, so that a high voltage can be applied, and therefore, a change due to voltage dependency of a driving voltage can also be reduced.

The driving current can be adjusted by changing the mirror ratio N of the NMOS transistors 21, 22 or the current value Ib of the current source 11, and a resistance ratio of the resistor 12 and the resistor 10 may be adjusted.

Control operations of the present embodiment are illustrated in FIG. 3. The control signal is a signal input to the switch 18. The switch is turned off at Low (L), and the gate terminal of the NMOS transistor 19 is connected to GND; the switch is turned on at High (H), and the gate terminal is connected to the driving voltage output from the driving signal generation unit 9. The driving current $I_{DRIVE}$ from the high voltage PMOS transistor 17 of the driving unit 7 is output by the NMOS transistor 19 connected to the driving voltage and is applied to the load resistor 20 and the transducer 8. Most of the driving currents flow through the transducer 8. As the driving current is applied, an output voltage Vout rises. When the output voltage Vout rises to near VDD1, the high voltage PMOS transistor 17 of the driving unit 7 is in a linear region, so that the current is only supplied to the load resistor. Meanwhile, when the control signal becomes L, the Ic becomes zero and the driving current $I_{DRIVE}$ becomes zero. Therefore, the charge charged in the transducer 8 is discharged by the load resistor 20 and the output voltage becomes zero. As a result, an ultrasonic transmission signal can be generated. In this embodiment, since the driving current $I_{DRIVE}$ output from the high voltage PMOS transistor 17 is constant, a slope of the output voltage Vout is constant.

A configuration example in which the driving signal generation unit 9 and the transmission circuit 102 of the present embodiment are applied to an ultrasonic diagnostic apparatus 300 is illustrated in FIG. 4. A control signal of the driving signal from a control unit 101 is transmitted to the driving signal generation unit 9, and a driving signal value is determined. The transmitted control signal is transmitted to the transmission circuit 102, and a transmission signal is formed by turning on and off the switch. The transmitted signal output from the transmission circuit 102 is converted into an ultrasound signal by an ultrasonic transducer 103 and performs irradiation on a living body. A reflected signal from the living body is received again by the ultrasonic transducer 103, is converted into an electrical signal, and is displayed as an ultrasonic image by a display unit 107 after being subjected to signal processing performed by a transmission-reception separating unit 104, a reception circuit 105, and an image processing unit 106. At this time, the transmission circuit 102, the transmission-reception separating unit 104, and the reception circuit 105 are disposed with the same number of a plurality of ultrasonic transducers 103. Only one driving signal generation unit 9 may be disposed in common for the plurality of transmission circuits 102. The plurality of transmission circuits 102 and the driving signal generation unit 9 may be formed on the same semiconductor.

The low voltage transistor and the high voltage transistor have large variations due to different semiconductor manufacturing processes, and according to the present embodiment, it is possible to provide an ultrasonic diagnostic apparatus in which the driving current of the ultrasonic transducer is constant with respect to semiconductor process variations of the low voltage transistor and the high voltage transistor.

Second Embodiment

The second embodiment of the invention is illustrated in FIG. 5. In the second embodiment, the transducer 8 can be supplied with a driving current that is inverted between positive and negative. The transmission circuit 102 includes a positive-side driving unit 7a and a negative-side driving unit 7b. A positive power source VDD1, a control signal a and a driving signal a are input to the positive-side driving unit 7a, and a negative power source VDD2, a control signal b and a driving signal b are input to the negative-side driving unit 7b. The driving signals a, b are respectively generated by driving signal generation units 9a, 9b. Outputs of the driving units 7a, 7b of the transmission circuit 102 and the transducer 8 are connected with each other.

FIG. 6 is an internal configuration diagram of FIG. 5. The driving signal generation unit 9a that generates the positive-side driving signal a and the positive-side driving unit 7a are those described in the first embodiment. In the driving signal generation unit 9b that generates the negative-side driving signal b, a current flowing from a PMOS transistor 31 to a resistor 23 is automatically adjusted by a feedback control, so that the reference current Ib of a current source 33 and a reference voltage Vob generated by a resistor 34, in a minus terminal of a difference detection unit 2b have the same potential as that in the first embodiment. When the resistor 34 and the resistor 23 are equal, a current flowing through the resistor 23 is Ib; and when a current mirror ratio of a negative-side current detection unit 5b is 1:N, a current flowing through a high voltage NMOS transistor 28 of a negative-side transmission circuit replica unit 4b is Ib×N. When a current mirror ratio of a low voltage NMOS transistor 27 and the high voltage NMOS transistor 28 in the negative-side transmission circuit replica unit 4b is Mb, Ib×N/Mb flows through a drain of the low voltage NMOS transistor 27, and a gate potential of a PMOS transistor 25 through which this current flows as in a positive side becomes the driving signal b, so that a driving current $I_{DRIVE2}$ of Ib×N flows through the negative-side driving unit 7b of the transmission circuit 102. Since this driving current is determined by the current mirror ratio N of the PMOS transistors 31, 32 as in the positive side, it is not affected by process variations of the semiconductor.

Next, operations of FIG. 6 will be described with reference to FIG. 7. The driving currents $I_{DRIVE1}$ and $I_{DRIVE2}$ flow when the control signal is turned on and off, as in the description of the first embodiment. A difference from the first embodiment is that an output can output three values of VDD1, VDD2, and zero. In FIG. 7(a), firstly, a control signal a becomes high, and the output becomes VDD1 from zero. Subsequently, the control signal a becomes Low and a control signal b becomes High. At this time, the output transitions from VDD1 to VDD2. Thereafter, when both the control signal a and the control signal b become Low, the output becomes zero. In FIG. 7(b), the control signal a and the control signal b are reversed and the outputs are also inverted. By transmitting these symmetrical waveforms alternately and adding the reception waveform, a fundamental wave component can be removed. For example, the VDD1 can be +50 V, the VDD2 can be −50 V, and VDD applied to the current source 33 and the current detection unit 5b can be +5 V.

FIG. 8 illustrates a conceptual diagram of pulse inversion. FIG. 8(a) illustrates a transmission waveform when no driving signal generation unit is provided and a positive-side driving current becomes smaller than a negative-side driving current due to the semiconductor process variations, and a residual component after the adding. When the positive-side driving current is reduced and a rise time is delayed, the residual components remain, which leads to deterioration of a diagnostic image. On the other hand, when the driving current is generated by the driving signal generation units 9a, 9b in FIG. 5, the driving current is constant, and therefore, as illustrated in FIG. 8(b), a positive-negative symmetrical transmission waveform is obtained, and the residual component is eliminated. As a result, high image quality of the ultrasonic image can be implemented.

Third Embodiment

The third embodiment of the invention is illustrated in FIG. 9. The third embodiment is an application example of the invention to ultrasonic diagnostic apparatus. The ultrasonic diagnostic apparatus 300 is configured with a main frame 201, an ultrasonic probe 203 connected to the main frame via a cable 202, and an image display unit 107. The ultrasonic transducer 103 is disposed in the ultrasonic probe 203, and the transmission circuit 102 disposed in the main frame 201 and the ultrasonic transducer 103 are connected via a wiring in the cable 202. At this time, the transmission circuit 102 and the driving signal generation unit 9 are disposed in the main frame 201. A plurality of ultrasonic transducers 103 and transmission circuits 102 may be disposed.

Fourth Embodiment

The fourth embodiment of the invention is illustrated in FIG. 10. The fourth embodiment is a second application example of the invention to the ultrasonic diagnostic apparatus. The ultrasonic diagnostic apparatus 300 is configured with the main frame 201, the ultrasonic probe 203 connected to the main frame via the cable 202, and the image display unit 107. The ultrasonic transducer 103, the transmission circuit 102 and the driving signal generation unit 9 are disposed in the ultrasonic probe 203.

At this time, the ultrasonic transducers 103 disposed in the ultrasonic probe 203 are arranged as a two-dimensional array in an M×N manner. As illustrated in FIG. 11, an analog front-end circuit 41 is connected to each ultrasonic transducer 103, and a three-dimensional ultrasonic image can be acquired by adjusting a timing of transmission and reception. The analog front end circuit 41 includes the transmission circuit 102 and the reception circuit 105 corresponding to each of the ultrasonic transducers 103. M× N analog front-end circuits 41 are formed on the same semiconductor and are integrated as a beam former IC 40 together with a delay control unit and an amplitude voltage generation unit (not shown). At this time, as illustrated in FIG. 11, the driving signal generation unit 9 is disposed outside the of the two-dimensional array of the M× N analog front-end circuits 41, and supplies a driving signal to a plurality of transmission circuits 102 in common. At this time, the driving signal may be sent by the same wiring being wired on the integrated circuit, or may be converted into a current temporarily, and after being sent as the current, it is returned to the driving signal again and input to the transmission circuit 102.

Fifth Embodiment

An ultrasonic diagnostic apparatus according to the fifth embodiment of the invention is illustrated in FIG. 12. In the fifth embodiment, an operation of the driving signal generation unit 9 is synchronized with an operation of the transmission circuit 102.

As illustrated in a diagram of an operation mode of FIG. 13, in the ultrasonic diagnostic apparatus, a transmission section TX during which a transmission circuit is operated to transmit an ultrasonic wave and a reception section RX during which a reflected ultrasonic wave is received are alternately repeated, so that an ultrasonic image is generated. In this embodiment, an operation control signal for turning the circuit on and off is input to the driving signal generation unit 9. The driving signal generation unit 9 performs an operation (calibration operation) only when an ON operation control signal is input, and stops the operation when an OFF operation control signal is input. As illustrated in FIG. 13, the calibration operation of the driving signal generation unit 9 is synchronized with the operation of the transmission circuit 102, and the operation of the driving signal generation unit 9 is performed only in the transmission section TX, so that an average power of the driving signal generation unit 9 is reduced and the power consumption can be reduced.

REFERENCE SIGN LIST

1: Reference voltage generation unit
2: Difference detection unit
3: Voltage-current conversion unit
4: Transmission circuit driving unit replica
5: Current detection unit
6: Current-voltage conversion unit
7: Transmission circuit driving unit
8: Transducer
9: Driving signal generation unit
10, 12: Resistor
11: Constant current source
13: OPAMP
14, 19: Transistor
15: High voltage transistor
16: Low voltage transistor
17: High voltage transistor
18: Switch
20: Load resistor
21, 22: Transistor
40: Beam former IC
41: Analog front-end circuit
101: Control unit
102: Transmission circuit
103: Ultrasonic transducer
104: Transmission-reception separating unit
105: Reception circuit
106: Image processing unit
107: Display unit
201: Main frame
202: Cable
203: Ultrasonic probe
300: Ultrasonic diagnostic apparatus

The invention claimed is:

1. An ultrasonic diagnostic apparatus comprising:
a transducer;
a driving signal generation unit configured to generate a driving signal; and
a transmission circuit configured to output a driving current corresponding to the driving signal, so as to drive the transducer, wherein
the transmission circuit includes:
a transducer driving unit formed by a current mirror with a low voltage transistor and a high voltage transistor, the high voltage transistor being connected with the transducer, and
a current source configured to supply an operation current corresponding to the driving signal to the low voltage transistor of the transducer driving unit,
the driving signal generation unit includes:
a transmission circuit driving unit replica that has a configuration same as that of the transducer driving unit, and
a feedback control unit configured to detect a current flowing through a high voltage transistor of the transmission circuit driving unit replica, and to control the current to be constant, and
a signal applied from the feedback control unit to a current source configured to supply an operation current to a low voltage transistor of the transmission circuit driving unit replica is supplied, as the driving signal, to the current source configured to supply the operation current to the low voltage transistor of the transducer driving unit.

2. The ultrasonic diagnostic apparatus according to claim 1, wherein
the current source is formed by a transistor configured to convert the driving signal into a current, a gate terminal of the transistor is provided with a switch configured to turn on and off an input of the driving signal based on a control signal, and a transmission signal is generated based on the driving signal and the control signal.

3. The ultrasonic diagnostic apparatus according to claim 1, wherein
a same power source voltage is applied to the current mirror with the low voltage transistor and the high voltage transistor of the transmission circuit and a current mirror with the low voltage transistor and the high voltage transistor of the transmission circuit driving unit replica.

4. The ultrasonic diagnostic apparatus according to claim 3, wherein
the low voltage transistor of the transmission circuit and the low voltage transistor of the transmission circuit driving unit replica are serially connected to the respective high voltage transistors.

5. The ultrasonic diagnostic apparatus according to claim 1, wherein
the feedback control unit includes:
a reference voltage generation unit configured to generate a reference voltage;
a current detection unit configured to detect a current flowing through the high voltage transistor of the transmission circuit driving unit replica;
a current-voltage conversion unit configured to convert the current detected by the current detection unit into a voltage;
a difference detection unit configured to compare the reference voltage generated by the reference voltage generation unit with the voltage converted by the current-voltage conversion unit, and to detect a difference; and a voltage-current conversion unit configured to convert the difference into a current, and to supply the current to the low voltage transistor of the transmission circuit driving unit replica.

6. The ultrasonic diagnostic apparatus according to claim 1, wherein
the driving signal generation unit is provided in common for a plurality of transmission circuits.

7. The ultrasonic diagnostic apparatus according to claim 1, wherein
the transmission circuit and the driving signal generation unit are formed on the same semiconductor.

8. The ultrasonic diagnostic apparatus according to claim 1, wherein
the transducer driving unit is formed by a positive-side driving unit including a PMOS transistor and a negative-side driving unit including a NMOS transistor, such that driving currents that are different between positive and negative is supplied to the transducer, and
the driving signal generation units configured to make a driving current to be constant are respectively disposed in the positive-side driving unit and the negative-side driving unit.

9. The ultrasonic diagnostic apparatus according to claim 8, wherein
the transducer driving unit supplies a driving current that is alternately inverted between positive and negative to the transducer, and
the transducer transmits an ultrasonic wave that is alternately inverted.

10. The ultrasonic diagnostic apparatus according to claim 9, wherein
a fundamental wave component is removed by alternately transmitting symmetrical waveforms of an ultrasonic wave and adding reception waveforms.

11. The ultrasonic diagnostic apparatus according to claim 1, wherein
the transducer is disposed in an ultrasonic probe,
the transmission circuit and the driving signal generation unit are disposed in a main frame, and
the ultrasonic probe and the main frame are connected with each other by a cable.

12. The ultrasonic diagnostic apparatus according to claim 1, wherein
the transducer, the transmission circuit and the driving signal generation unit are disposed in an ultrasonic probe.

13. The ultrasonic diagnostic apparatus according to claim 12, further comprising:
M×N transducers arranged in a two-dimensional array;
M×N analog front-end circuits each including a transmission circuit and respectively corresponding to the transducers; and
a driving signal generation unit configured to supply a driving signal to a plurality of transmission circuits.

14. The ultrasonic diagnostic apparatus according to claim 13, wherein
the M×N analog front-end circuits and the driving signal generation unit are formed on the same semiconductor.

15. The ultrasonic diagnostic apparatus according to claim 1, wherein
a transmission operation of the transmission circuit and a calibration operation of the driving signal generation unit are performed in synchronization, and the driving signal generation unit is operated only in a transmission section.

* * * * *